United States Patent [19]

Eibeck et al.

[11] Patent Number: 5,948,381

[45] Date of Patent: *Sep. 7, 1999

[54] PROCESS FOR SEPARATING FLUOROCARBON COMPOUNDS

[75] Inventors: Richard Elmer Eibeck, Orchard Park; Hang Thanh Pham, Amherst; Valentine Theodore Zuba, Orchard Park, all of N.Y.

[73] Assignee: AlliedSignal Inc., Morristown, N.J.

[ * ] Notice: This patent is subject to a terminal disclaimer.

[21] Appl. No.: 08/675,022

[22] Filed: Jul. 3, 1996

[51] Int. Cl.$^6$ .............................. C01B 7/19; C07C 17/38
[52] U.S. Cl. ........................ 423/484; 570/177; 570/178
[58] Field of Search ............................... 423/483, 484; 570/177, 178

[56] References Cited

U.S. PATENT DOCUMENTS

| | | | |
|---|---|---|---|
| 3,873,629 | 3/1975 | Jones | 260/653 |
| 3,947,558 | 3/1976 | Van Eijl | 423/483 |
| 3,976,447 | 8/1976 | Merchant et al. | 55/71 |
| 4,102,981 | 7/1978 | Woychesin et al. | 570/177 |
| 4,209,470 | 6/1980 | Lorquet | 260/652 |
| 4,911,792 | 3/1990 | Manzer et al. | 203/39 |
| 5,196,616 | 3/1993 | Lee et al. | 423/483 |
| 5,211,020 | 5/1993 | Taylor et al. | 62/11 |
| 5,211,817 | 5/1993 | Adams et al. | 203/82 |
| 5,426,254 | 6/1995 | Galland et al. | 423/483 |
| 5,458,674 | 10/1995 | Barsotti | 95/122 |
| 5,560,899 | 10/1996 | Solinas et al. | 570/177 |
| 5,632,966 | 5/1997 | Van Der Puy et al. | 423/483 |
| 5,789,633 | 8/1998 | Beug-Deeb et al. | 570/178 |
| 5,800,795 | 9/1998 | Ryan et al. | 423/484 |

FOREIGN PATENT DOCUMENTS

| | | | |
|---|---|---|---|
| 592711 | 4/1994 | European Pat. Off. | 570/177 |
| 4311062 | 10/1994 | Germany | 570/177 |
| 19248 | 6/1972 | Japan | 570/177 |

OTHER PUBLICATIONS

WO94/20412, Sep 15, 1994.
A.I. Vogel, *A Textbook of Practial Organic Chemistry*, Third Edition, 1956. p. 151.
S. Glasstone, *Textbook of Physical Chemistry*, Second Edition, 1946. pp. 729–730.
W.F. Linke, *Solubilities. Inorganic and Metal–Organic Compounds*, 1965. pp. 210–211, 1030–1031.

*Primary Examiner*—Wayne Langel
*Attorney, Agent, or Firm*—Jay P. Friedenson; Marie L. Collazo

[57] ABSTRACT

The invention provides a process for separating fluorinated organic compounds from mixtures of the such compounds and hydrogen fluoride. More particularly, the invention provides a method for separating a fluorinated organic compound from a mixture containing at least one fluorinated organic compound and hydrogen fluoride by adding an inorganic salt to the mixture.

21 Claims, No Drawings

PROCESS FOR SEPARATING FLUOROCARBON COMPOUNDS

FIELD OF THE INVENTION

This invention relates to a process for separating fluorinated organic compounds from mixtures of the such compounds and hydrogen fluoride. More particularly, the invention provides a method for separating a fluorinated organic compound from a mixture containing at least one fluorinated organic compound and hydrogen fluoride by adding an inorganic salt to the mixture.

BACKGROUND OF THE INVENTION

A number of well known methods for the production of fluorinated organic compounds utilize reactions in which the fluorine donating compound is hydrogen fluoride. The products of these reactions are difficult to recover because hydrogen fluoride is highly soluble in the fluorinated organic compounds and forms azeotropic and azeotrope-like mixtures with many of these compounds. Therefore a number of methods have been developed to separate and recover organic fluorinated compounds from a mixture of these compounds and hydrogen fluoride.

The known methods include the use of aqueous alkali solutions, glycol, alkaline earth compounds, carbon molecular sieves, distillation, and membranes to facilitate separation. However, each of these methods is disadvantageous in that they are multi-step processes that produce toxic waste disposal problems or require specialized equipment. Thus, a need exists for a separation method that attempts to overcome some of the disadvantages of the prior art methods.

DESCRIPTION OF THE INVENTION AND PREFERRED EMBODIMENTS

This invention provides a process for separating fluorinated organic compounds from mixtures of such compounds and hydrogen fluoride. The process of the invention comprises adding an inorganic salt to a mixture of at least one fluorinated organic compound and hydrogen fluoride in order to form a product mixture having an organic phase and an inorganic phase. The organic phase may be recovered from the product mixture. Further, the organic phase may be purified to provide a pure fluorinated organic compound and/or the hydrogen fluoride and inorganic salt separated for reuse. The process of the invention provides a simple and economical method for separating a fluorinated organic compound from hydrogen fluoride.

Fluorinated organic compounds that may be separated by the process of the invention include, without limitation, chlorofluorocarbons, hydrochlorofluorocarbons, hydrofluorocarbons, perfluorocarbons, and mixtures thereof The invention may be used for separating liquid phase mixtures of fluorinated organic compounds and hydrogen fluoride and may be used in batch, continuous, and intermittent modes.

The mixture of fluorinated organic compound and hydrogen fluoride may be any such mixture including azeotropic or azeotrope-like mixtures. For purposes of this invention, azeotrope-like mixtures are mixtures that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the state pressure and temperature. In practice, this means that the components of an azeotropic mixture are constant boiling and cannot be separated during a phase change.

Azeotrope-like mixtures behave like azeotropic mixtures, i.e., or are constant boiling or essentially constant boiling. In other words, for azeotrope-like compositions, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree.

The process of the invention is carried out in any suitable corrosion resistant vessel. In the process, an inorganic salt is added to a mixture of at least one fluorinated organic compound and hydrogen fluoride in order to produce a product mixture having an organic phase and an inorganic phase. The organic phase contains the fluorinated organic compound and the inorganic phase the hydrogen fluoride and inorganic salt.

Inorganic salts suitable for use in the process of the invention are alkali metal fluoride and bifluoride salts. Exemplary fluoride and bifluoride salts include, without limitation, sodium fluoride and bifluoride, potassium fluoride, bifluoride, and mixtures thereof Preferably, sodium fluoride or potassium fluoride is used.

Conditions of temperature and pressure are not critical to the process of the invention. Therefore, the process may be carried out at the same conditions used to form the fluorinated organic compound/hydrogen fluoride mixture. The amount of inorganic salt used will depend on the solubility of the inorganic salt in the hydrogen fluoride. Solubilities for potassium and fluoride salts can be found in William F. Linke, II *Solubilities of Inorganic and Metal-Organic compounds* (1965). Generally, a hydrogen fluoride to inorganic salt ratio of from about 1:1 to about 8:1, preferably from about 2:1 to about 8:1, is used.

On addition of the inorganic salt to the fluorinated organic compound/hydrogen fluoride mixture, a two phase product mixture immediately forms. The hydrogen fluoride is almost completely confined to the inorganic phase and the fluorinated compound to the organic phase. In a further step of the process, the organic phase may be recovered from the product mixture. Recovery may be performed using any convenient means known in the art such as decantation or filtration.

Additionally, the organic phase recovered may be purified in yet a further step to provide a pure fluorinated organic compound. Purification may be accomplished by any convenient means such as distillation. Still further, the hydrogen fluoride and inorganic salt may be separated by any convenient means, such as evaporation of the hydrogen fluoride, and reused.

The invention will be clarified further by a consideration of the following non-limiting examples.

EXAMPLES

Example 1

In a PFA™ cell, 40 g of 1,1,1,3,3,5,5,5-octafluoropentane, 458 mfcf, were dissolved in 60 g HF and an azeotropic mixture was formed as shown by vapor liquid equilibrium measurements. 12 g of potassium fluoride were added to and dissolved in the octafluoropentane/HF mixture and upper and lower phases formed immediately. The cell was submerged in a constant temperature bath at $-11°$ C. The temperature of the bath was gradually increased and, at various temperatures the volume percent of the upper and lower phases were determined. Up to 45° C., the mixture still had two phases. At room temperature, the upper and lower phases were separated and sampled for analysis. Ion chromatography ("IC") was used to determine the composition of the phases. The results are recorded on Table 1.

TABLE 1

| Temperature (°C.) | Volume % Lower/Upper Phase (±2%) | Phase Composition (wt %) HF/KF1458 mfcf at 23° C. |
|---|---|---|
| −11 | 40/60 | — |
| 0 | 40/60 | — |
| 23 | 36/64 | — |
| 35 | 36/64 | — |
| 45 | 36/64 | — |
| Upper Phase | — | 78.08/14.37/7.55 |
| Bottom Phase | — | 1.56/0.03/98.41 |

Example 1 demonstrates that upon addition of the inorganic salt to the HF/octafluoropentane azeotrope, a two phase system is formed in which the hydrogen fluoride is almost totally confined to the inorganic phase.

Example 2

75 g 1,1,1,3,3-pentafluoropropane, 245 fa, were dissolved in 25 g HF to form a homogeneous azeotropic solution. 11 g potassium fluoride were added to the solution causing the mixture to separate immediately into an upper and lower phase. The lower phase was decanted into a PFA cell and each layer was sampled and analyzed. IC and atomic absorption spectrophotometer showed that the upper phase was composed of 0.2 wt percent KF, 0.6 wt percent HF, and 99.2 wt percent 245 fa. The lower phase was composed of 21.1 wt percent KF, 48.4 wt percent HF and 30.5 wt percent 245 fa.

Example 3

40 g of 458 mfcf are dissolved in 60 g HF and an azeotropic mixture formed. 12 g potassium bifluoride are added and dissolved into the mixture and upper and lower phases form immediately. HF is evaporated from the upper phase, condensed using dry ice and collected. The lower phase is washed once with an amount of water equal to the amount of HF to remove trace HF and provide pure octafluoropentane.

Example 4

75 g 245 fa are dissolved in 25 g HF to form a homogeneous azeotropic solution. 11 g potassium bifluoride are added to the solution causing an upper and lower phase to form immediately.

What is claimed is:

1. A process for separating a fluorinated organic compound from a liquid phase mixture containing a fluorinated organic compound and hydrogen fluoride which comprises adding an inorganic salt selected from the group consisting of sodium fluoride, sodium bifluoride, potassium fluoride, potassium bifluoride and mixtures thereof to a mixture comprising at least one fluorinated organic compound and hydrogen fluoride in order to form a product mixture having an organic phase comprising the at least one fluorinated organic compound and an inorganic phase comprising hydrogen fluoride and the inorganic salt.

2. The process of claim 1 further comprising the step of recovering the organic phase from the product mixture.

3. The process of claim 2 further comprising the step of purifying the organic phase recovered from the product mixture.

4. The process of claim 3 further comprising the step of separating the hydrogen fluoride and inorganic salt.

5. The process of claim 1 wherein the liquid phase mixture of the at least one fluorinated compound and the hydrogen fluoride is an azeotropic mixture.

6. The process of claim 1 wherein the inorganic salt is sodium fluoride.

7. The process of claim 1 wherein the inorganic salt is potassium fluoride.

8. The process of claim 1 wherein a weight ratio of hydrogen fluoride to inorganic salt of from about 1:1 to about 8:1 is used.

9. The process of claim 5 wherein a weight ratio of hydrogen fluoride to inorganic salt of from about 1:1 to about 8:1 is used.

10. The process of claim 6 wherein a weight ratio of hydrogen fluoride to inorganic salt of from about 1:1 to about 8:1 is used.

11. The process of claim 9 wherein a weight ratio of hydrogen fluoride to inorganic salt of from about 1:1 to about 8:1 is used.

12. The process of claim 1 wherein the fluorinated compound is 1,1,1,3,3,5,5,5-octafluoropentane.

13. The process of claim 5 wherein the fluorinated compound is 1,1,1,3,3,5,5,5-octafluoropentane.

14. The process of claim 1 wherein the fluorinated compound is 1,1,1,3,3-pentafluoropropane.

15. The process of claim 5 wherein the fluorinated compound is 1,1,1,3,3-pentafluoropropane.

16. A process for separating a fluorinated organic compound from a liquid phase mixture containing a fluorinated organic compound and hydrogen fluoride comprising the steps of adding an alkali metal fluoride salt selected from the group consisting of sodium fluoride, sodium bifluoride, potassium fluoride, potassium bifluoride and mixtures thereof to an azeotrope-like liquid phase mixture of 1,1,1, 3,3,5,5,5-octafluoropropane and hydrogen fluoride, in a weight ratio of hydrogen fluoride to alkali metal fluoride salt of from about 1:1 to about 8:1, in order to form a product mixture having an organic phase and an inorganic phase; recovering the organic phase from the product mixture; and purifying the organic phase recovered from the product mixture.

17. The process of claim 16 wherein the alkali metal fluoride salt is sodium fluoride.

18. The process of claim 16 wherein the alkali metal fluoride salt is potassium fluoride.

19. A process for separating a fluorinated organic compound from a liquid phase mixture containing a fluorinated organic compound and hydrogen fluoride comprising the steps of adding an alkali metal fluoride salt selected from the group consisting of sodium fluoride, sodium bifluoride, potassium fluoride, potassium bifluoride and mixtures thereof to an azeotrope-like liquid phase mixture of 1,1,1, 3,3-pentafluoropropane and hydrogen fluoride, in a weight ratio of hydrogen fluoride to alkali metal fluoride salt of from about 1:1 to about 8:1, in order to form a product mixture having an organic phase and an inorganic phase; recovering the organic phase from the product mixture; and purifying the organic phase recovered from the product mixture.

20. The process of claim 19 wherein the alkali metal fluoride salt is sodium fluoride.

21. The process of claim 19 wherein the alkali metal fluoride salt is potassium fluoride.

* * * * *